United States Patent [19]
Ahrens et al.

[11] 3,960,949
[45] June 1, 1976

[54] 1,2-BIGUANIDES

[75] Inventors: Hanns Ahrens; Clemens Rufer; Helmut Biere; Eberhard Schröder; Wolfgang Losert; Olaf Loge; Ekkehard Schillinger, all of Berlin, Germany

[73] Assignee: Schering Aktiengesellschaft, Berlin & Bergkamen, Germany

[22] Filed: July 9, 1974

[21] Appl. No.: 486,758

Related U.S. Application Data

[63] Continuation of Ser. No. 239,923, March 31, 1972, abandoned.

[30] Foreign Application Priority Data

Apr. 2, 1971  Germany............................ 2117015

[52] U.S. Cl. .................. 260/564 B; 260/239 AA; 260/247.5 R; 260/268 R; 260/293.87; 260/307 R; 260/307 F; 260/326.86
[51] Int. Cl.² ........................................ C07C 129/16
[58] Field of Search .......... 260/564 B, 565, 501.14, 260/295.55

[56] References Cited
UNITED STATES PATENTS

3,170,925   2/1965   Doub.............................. 260/564 B

FOREIGN PATENTS OR APPLICATIONS

637,147   1962   Canada............................ 260/565

OTHER PUBLICATIONS

Chem. Abstr., vol. 49, col. 14,186(d) (1955).
Chem. Abstr., vol. 43, col. 3793(b) (1949).
Chem. Abstr., vol. 43, col. 9039(i) (1949).
Chem. Abstr., vol. 57, col. 16,618(a) (1962).

*Primary Examiner*—Gerald A. Schwartz
*Attorney, Agent, or Firm*—Millen, Raptes & White

[57] ABSTRACT

1,2-Substituted biguanides of the formula

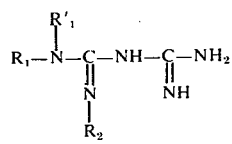

wherein $R_1$ is saturated or unsaturated, straight-chain or branched hydrocarbon of 1–12 carbon atoms which is unsubstituted or substituted by one or more fluorine atoms; a cycloalkyl group of 3–6 carbon atoms; or an aryl or aralkyl group of the formula

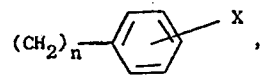

with $n$ being the integer 0, 1 or 2 and X being hydrogen or halogen; and $R'_1$ is a hydrogen atom or a saturated or unsaturated, straight-chain or branched hydrocarbon group of 1–12 carbon atoms; or $R_1$ and $R'_1$ collectively with the nitrogen atom to which they are attached are a heterocyclic ring containing one or more hetero atoms; and $R_2$ is saturated or unsaturated, straight-chain or branched hydrocarbon of 1–12 carbon atoms which is unsubstituted or substituted by one or more fluorine atoms; or cycloalkyl of 3–6 carbon atoms, alkoxyalkyl containing a total of 2–12 carbon atoms, or alkoxy of 1–6 atoms; mixtures thereof, and pharmaceutically acceptable acid addition salts thereof, are useful in the treatment of diabetes mellitus.

7 Claims, No Drawings

1,2-BIGUANIDES

This is a continuation of application Ser. No. 239,923 filed March 31, 1972, now abandoned.

BACKGROUND OF THE INVENTION

This invention relates to substituted biguanides suitable for diabetes mellitus therapy.

Three compounds of the class of substituted biguanides are utilized for the treatment of diabetes mellitus, viz., 1-butylbiguanide, 1-β-phenethylbiguanide (phenformin), and 1,1-dimethylbiguanide (metformin). A characteristic of these three compounds is their narrow therapeutic spectrum and their gastrointestinal incompatibility.

It has now been found that the novel 1,2-substituted biguanides of the invention possess as good or better blood-sugar-lowering effect than the above-mentioned commercial products, and a better therapeutic index. For example, the $LD_{50}$ in mice of 1-butylbiguanide is 346 mg./kg., whereas the novel 1,2-biguanides can be tolerated without damage in doses of about 2 g./kg.

SUMMARY OF THE INVENTION

The invention provides novel 1,2-substituted biguanides of the general Formula I

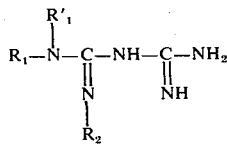

wherein $R_1$ is saturated or unsaturated, straight-chain or branched hydrocarbon of 1–12 carbon atoms which is unsubstituted or substituted by one or more fluorine atoms; a cycloalkyl group of 3–6 carbon atoms; or an aryl or aralkyl group of the formula

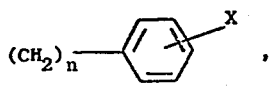

with n being the integer 0, 1 or 2 and X being hydrogen or halogen; and $R'_1$ is a hydrogen atom or a saturated or unsaturated, straight-chain or branched hydrocarbon group of 1–12 carbon atoms; or $R_1$ and $R'_1$ collectively with the nitrogen atom to which they are attached are a heterocyclic ring containing one or more hetero atoms; and $R_2$ is saturated or unsaturated, straight-chain or branched hydrocarbon of 1–12 carbon atoms which is unsubstituted or substituted by one or more fluorine atoms; or cycloalkyl of 3–6 carbon atoms, alkoxyalkyl containing a total of 2–12 carbon atoms, or alkoxy of 1–6 carbon atoms; mixtures thereof and pharmaceutically acceptable acid addition salts thereof.

In a composition aspect, this invention relates to pharmaceutical compositions comprising at least one compound of Formula I and a pharmaceutically acceptable carrier. In a method of use aspect, this invention relates to a method for the treatment of diabetes mellitus which comprises administering to the diabetic patient an effective blood-sugar-lowering amount of at least one compound of claim 1.

DETAILED DISCUSSION

Of the compounds of this invention, the following classes are preferred:

a. pharmaceutically acceptable acid addition salts thereof, especially the nitrates, hydrochlorides and hydrobromides;

b. one, two or all three of $R_1$, $R'_1$ and $R_2$ are alkyl, preferably of 1–8 carbon atoms, at least one preferably being methyl or ethyl, especially those of (a);

c. those of (b) wherein one of $R_1$, and $R_2$, preferably $R_2$, is cycloalkyl;

d. those of (b) wherein $R_1$ is phenyl, benzyl or phenethyl, unsubstituted or substituted;

e. those of (b) wherein one of $R_1$, $R'_1$ and $R_2$, preferably $R_2$, is unsaturated alkyl of up to 6 carbon atoms;

f. those of (b) wherein one of $R_1$, and $R_2$, preferably $R_2$ is cycloalkyl;

g. those of (b) wherein $R_2$ is alkoxy;

h. those of (b) wherein one of $R_1$, and $R_2$, preferably $R_2$, is fluorosubstituted alkyl, preferably those containing 1–8 fluorine atoms;

i. those of (b) wherein $R_2$ is alkoxyalkyl;

j. those of Formula I wherein $R_1$ and $R'_1$ together with the nitrogen atom represent a heterocyclic ring preferably piperidino, pyrrolidino, aziridino, morpholino, piperazine, oxazolino, oxazolidino.

The compounds are isolated as mono- or di-salts with mineral acids. The free bases of Formula I can be liberated from the salts thereof by means of a strong base and can, if desired, be converted into another salt by means of an acid.

The novel compounds are prepared as follows:

a. a thiourea of the general Formula II

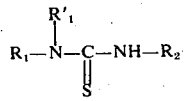

wherein $R_1$, $R'_1$, and $R_2$ have the above-indicated meanings, is reacted, in the presence of a metal or a metallic oxide, with guanidine or a salt of guanidine; or an isothiourea of the general Formula III

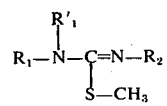

wherein $R_1$, $R'_1$ and $R_2$ have the above-indicated meanings, is reacted, in the presence of a tertiary amine, with guanidine or a salt of guanidine;

or a carbodiimide of the general Formula IV

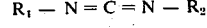

wherein $R_1$ and $R_2$ have the above-indicated meanings, is reacted with guanidine or a salt of guanidine; or b. a guanyl thiourea of the general Formula V

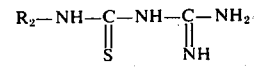

wherein $R_2$ has the above-indicated meanings, or the salt thereof, is reacted, in the presence of a heavy metal salt as well as optionally in the presence of a tertiary amine, with an amine of the general Formula VII

wherein $R_1$ and $R'_1$ have the above-indicated meanings; or a guanyl isothiourea of the general Formula VI

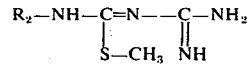

wherein $R_2$ has the above-indicated meanings, or the salt thereof, is reacted with an amine of Formula VII, above; or c. a cyanoguanidine of the general Formula VIII

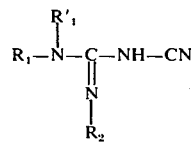

wherein $R_1$, $R'_1$, and $R_2$ have the above-indicated meanings, is reacted with an ammonium salt in a high-boiling solvent at an elevated temperature;

and optionally, the free base of Formula I is liberated with a strong base from the acid addition salts obtained in accordance with (a) through (c) and/or optionally the free base is converted into the acid addition salts with inorganic or organic acids.

The reactions according to (a) and (b) are generally carried out in solvents. Examples for suitable solvents are: alcohols, such as methanol, ethanol, n-propanol, isopropanol, or ethylene glycol; cyclic ethers, such as tetrahydrofuran or dioxane; hydrocarbons, such as nitrobenzene or anisole; furthermore dimethylformamide and dimethyl sulfoxide; but also water. It is likewise possible to use solvent mixtures.

Examples for suitable metals or metallic oxides in the reaction of a thiourea with guanidine according to (a) are: Raney nickel, lead oxide, and mercury oxide. The duration of the reaction depends on the reaction temperature. The temperature can be extensively varied. Thus, it is possible to operate at room temperature, but also at a higher temperature, e.g. at 30°–180° C.

The reaction of an isothiourea with guanidine according to (a) is effected in the presence of a tertiary amine at elevated temperatures, especially at 100°–150° C.

A tertiary amine is understood to mean all conventional tertiary amines, such as, for example, triethylamine, trimethylamine, ethyl diisopropylamine, azabicyclononane, pyridine, quinoline, etc.

Also, during the reaction of a guanyl thiourea with an amine according to (b), an addition of a tertiary amine proved to be advantageous.

As examples for a heavy metal salt in the reaction of a guanyl thiourea according to (b), it is possible to mention silver nitrate or mercury (II) chloride. The reaction is accomplished in a temperature range from −50° C. to +100° C., preferably at about −20° C. to +50° C.

If it is intended to react a carbodiimide with guanidine, according to (a), or a guanyl isothiourea with an amine, according to (b), higher temperatures must be employed, preferably temperatures up to the boiling point of the respective solvent or solvent mixture. Starting with the carbodiimide, it is only possible to produce 1,2-disubstituted biguanides.

A cyanoguanidine of the general Formula VIII is reacted, in accordance with (c) of this invention, with an ammonium salt in a high-boiling solvent at an elevated temperature. Examples for suitable ammonium salts are ammonium chloride, nitrate, sulfate, phosphate, etc. Examples for high-boiling solvents are nitrobenzene, anisole, dimethyl sulfoxide, o-dichlorobenzene, and hexamethylphosphoric triamide. The reaction takes place at temperatures of above 100° C., preferably between 110° and 150° C.

The novel 1,2-substituted biguanides possess an at least equally high blood-sugar-lowering effect as the known 1-substituted biguanides. However, the novel substances are superior to the known compounds in that they exhibit a lower toxicity.

In order to determine the toxicity in accordance with Karber (L. Ther. Grundlagen der experimentellen Arzneimittelforschung, Wiss. Verlagsgesellschaft [publishers], Stutthart (1965) 77–79), the acid addition salts were dissolved in water and administered orally in varying doses to groups of respectively three mice. Five days after administration of the substance, the number of surviving animals was determined. In the following table, the $LD_{50}$ values of several compounds of this invention are compared with the $LD_{50}$ values of phenformin and 1-butylbiguanide. The $LD_{50}$ values were in each case based on the free base.

| Substance | $LD_{50}$ [g./kg.] |
| --- | --- |
| 1,2-Diisopropylbiguanide | >2 |
| 1-Ethyl-2-n-butylbiguanide | >2 |
| 1-Methyl-2-$\beta$-phenethylbiguanide | 2.834 |
| 1,1,2-Triethylbiguanide | >2 |
| 1-Methyl-2-n-propylbiguanide | >2 |
| Phenformin | 0.55 |
| 1-Butylbiguanide | 0.346 |

The novel effective agents or the pharmaceutically acceptable salts thereof can be administered orally. For the formation of the salt, it is possible to utilize physiologically compatible inorganic or organic acids, such as, for example, hydrochloric acid, hydrobromic acid, nitric acid, sulfuric acid, phosphoric acid, methanesulfonic acid, p-toluenesulfonic acid, napththalene-1,5-disulfonic acid, acetic acid, lactic acid, succinic acid, tartaric acid, maleic acid, and nicotinic acid.

The substances can be processed without additives or with the additives, vehicles, flavor-ameliorating agents, and similar substances customary in galenic pharmacy, namely, for example, into the form of powders, as tablets, dragees, capsules, pills, or in the form of suspensions or solutions.

Suitable forms of dosage units, such as dragees or tablets, contain preferably 5–200 mg. of the effective agent of this invention. They can be administered to diabetic patients in substantially the same manner as the known compounds phenformin, metformin and 1-butylbiguanide. Even though the known compounds possess a relatively little toxicity in relation to the unit dosage the compounds of the present invention are significantly advantageous because the diabetes mellitus therapy is a long time therapy, i.e., the active substances have to be administered for a very long period.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in anyway whatsoever.

EXAMPLE 1

1,2-Diisopropylbiguanide Hydrobromide 22.9 g. (240 millimols) of guanidine hydrochloride in 240 ml. of absolute ethanol is added to a solution of 5.52 g. (240 mmol) of sodium in 240 ml. of absolute ethanol. The thus-precipitated sodium chloride is centrifuged, the guanidine solution is decanted, and mixed, under agitation, with 38.4 g. (240 mmol) of diisopropyl thiourea and 110 g. (500 mmol) of yellow mercury oxide. The reaction mixture is stirred for 60 hours, filtered, mixed with 64% strength hydrobromic acid up to a pH of 4, and concentrated at 35° C. to about 150 ml.

The crystalline crude product is washed with cold ethanol and once recrystallized from hot ethanol.

Yield: 17.6 g. = 28% of theory; m.p. 247°–248° C.

EXAMPLE 2

1,2-Diethylbiguanide Hydrobromide

The compound is produced analogously to Example 1 with diethyl thiourea. Yield: 32% of theory; m.p. 204° C. (from ethanol).

EXAMPLE 3

1,2-Di-n-butylbiguanide Hydrochloride 0.715 g. (7.5 mmol) of guanidine hydrochloride, 1.54 g. (10 mmol) of di-n-butyl carbodiimide, 5 ml. of water, and 15 ml. of methanol is heated for 16 hours under reflux. After evaporation, the oily residue is taken up in 15 ml. of water and extracted three times with respectively 20 ml. of ether in order to remove the 1,2-di-n-butyl urea formed as a by-product. The aqueous phase is mixed with concentrated hydrochloric acid to a pH of 4 and crystallizes during evaporation. The crude product having a melting point of 102°–105° C. is still contaminated by guanidine hydrochloride and minor amounts of 1,2-di-n-butyl urea. The product is suspended in dry chloroform, the remaining guanidine hydrochloride is filtered off, the chloroform solution is concentrated by evaporation, and the solid residue is recrystallized from acetonitrile.

Yield: 0.42 g. = 23% of theory; m.p. 131°–133° C.

EXAMPLE 4

1,2-Di-n-butylbiguanide Hydrochloride 1.88 g. (10 mmol) of 1,2-di-n-butyl thiourea is dissolved in 10 ml. of absolute ethanol and heated with an excess (4.7 g.) of methyl chloride in an autoclave to 90° C. for 12 hours. After cooling, the reaction mixture is evaporated to dryness, and the thus-formed 1,2-di-n-butyl-S-methyl isothiourea hydrochloride is mixed with 0.95 g. (10 mmol) of guanidine hydrochloride and 20 ml. of triethylamine and heated in an autoclave to 120° C. for 6 hours. The crude product is evaporated to dryness, and the solid residue is extracted three times with respectively 20 ml. of dry chloroform. The chloroform extracts are evaporated, and the solid residue is recrystallized from acetonitrile.

Yield: 1.13 g. = 45% of theory; m.p. 131°–132° C. (from acetonitrile).

EXAMPLE 5

1-Ethyl-2-(2-methylbutyl)-biguanide Nitrate 17.7 g. (100 mmol) of 1-ethyl-3-guanyl thiourea carbonate is dissolved in the hot state in 400 ml. of ethanol, mixed at 10° C. with 19.2 g. (220 mmol) of 2-methylbutylamine, and cooled to 0°–5° C. At 15° C., within one hour, 38 g. (220 mmol) of silver nitrate in 1400 ml. of ethanol is added thereto, and the mixture is agitated for 30 minutes at room temperature. Any excess silver ions are removed by using hydrogen sulfide as the sulfide compound, and the filtrate is concentrated to dryness. The crude product is recrystallized from a small quantity of water and then from acetonitrile.

Yield: 8.7 g. = 33% of theory; m.p. 133.5°– 134.5° C.

EXAMPLE 6

1,1-Dimethyl-2-ethylbiguanide Nitrate

The compound is produced analogously to Example 5, using dimethylamine.

Yield: 36% of theory; m.p. 159°–160° C. (from ethanol).

EXAMPLE 7

2-Methyl-1,1-diethylbiguanide Nitrate

The compound is produced analogously to Example 5 from 1-methyl-3-guanyl thiourea and diethylamine.

Yield: 6% of theory; m.p. 133° C. (from acetonitrile/ether).

EXAMPLE 8

2-Ethyl-1-methyl-1-isopropylbiguanide Nitrate

The compound is prepared analogously to Example 5 with methylisopropylamine.

Yield: 27% of theory; m.p. 161°–162° C. (from acetonitrile).

EXAMPLE 9

2-Methyl-1-methyl-1-phenylbiguanide Nitrate 16.3 g. (100 mmol) of 1-methyl-3-guanyl thiourea carbonate is dissolved hot in 400 ml. of ethanol, mixed at 10° C. with a mixture of 10.7 g. (100 mmol) of N-methylaniline and 12.1 g. (120 mmol) of triethylamine, and cooled to 0°–5° C. The addition of 220 mmol of silver nitrate and the further working-up procedure take place as described in Example 5. The triethylammonium nitrate, formed as a by-product, remains in solution during the recrystallization and thus is easily removed from the reaction mixture.

Yield: 32% of theory; m.p. 188° C. (from ethanol).

EXAMPLE 10

1-Methyl-2-(2-methylbutyl)-biguanide Nitrate

The compound is produced analogously to Example 5 from 1-methyl-3-guanyl thiourea and 2-methylbutylamine.

Yield: 51% of theory; m.p. 88°–90° C. (from acetonitrile).

EXAMPLE 11

2-Methyl-1-p-chlorophenylbiguanide Nitrate

The compound is produced analogously to Example 5 from 1-methyl-3-guanyl thiourea and p-chlorophenylaniline.

Yield: 24% of theory; m.p. 136°–137° C. (from water).

EXAMPLE 12

2-Methyl-1-p-chlorobenzylbiguanide Nitrate

The compound is prepared analogously to Example 5 from 1-methyl-3-guanyl thiourea and p-chlorobenzylamine.

Yield: 8% of theory; m.p. 152° C. (from acetonitrile).

EXAMPLE 13

2-Methyl-1-β-phenethylbiguanide Nitrate

This compound is produced analogously to Example 5 from 1-methyl-3-guanyl thiourea and β-phenethylamine.

Yield: 27% of theory; m.p. 117°–118° C. (from ethanol).

EXAMPLE 14

1,1,2-Triethylbiguanide Nitrate

The compound is produced analogously to Example 5 with diethylamine.

Yield: 22% of theory; m.p. 183°–184° C. (from ethanol).

EXAMPLE 15

2-Ethyl-1,1-di-n-propylbiguanide Nitrate

The compound is prepared analogously to Example 5 with di-n-propylamine.

Yield: 38% of theory; m.p. 166°–167° C. (from ethanol).

EXAMPLE 16

2-Ethyl-1,1-di-n-butylbiguanide Nitrate

The compound is produced analogously to Example 5 with di-n-butylamine.

Yield: 50% of theory; m.p. 140° C. (from acetonitrile).

EXAMPLE 17

1,1-Diethyl-2-allylbiguanide Nitrate

The compound is produced analogously to Example 5 from 1-allyl-3-guanyl thiourea and diethylamine.

Yield: 8% of theory; m.p. 154° C. (from ethanol-petroleum ether).

EXAMPLE 18

1-Ethyl-2-n-propylbiguanide Nitrate

The compound is produced analogously to Example 5 with n-propylamine.

Yield: 11% of theory; m.p. 134° C. (from acetonitrile).

EXAMPLE 19

1-Ethyl-2-cyclopropylbiguanide Nitrate

This compound is prepared analogously to Example 5 with cyclopropylamine.

Yield: 29% of theory; m.p. 118°–119° C. (from acetonitrile).

EXAMPLE 20

1-Ethyl-2-n-butylbiguanide Nitrate

This compound is produced analogously to Example 5 with n-butylamine.

Yield: 28% of theory; m.p. 99° C. (from ethyl acetate-ethanol).

Recrystallization from ethanol in the presence of a small amount of concentrated nitric acid results in the dinitrate, m.p. 164°–165° C.

EXAMPLE 21

1-Ethyl-2-sec.-butylbiguanide Nitrate

The compound is produced analogously to Example 5 with sec.-butylamine.

Yield: 20% of theory; m.p. 183° C. (from acetonitrile).

EXAMPLE 22

1-Ethyl-2-isobutylbiguanide Nitrate

The compound is produced in analogy to Example 5 with isobutylamine.

Yield: 18% of theory; m.p. 138°–139° C. (from acetonitrile).

EXAMPLE 23

1-Ethyl-2-tert.-butylbiguanide Nitrate

The compound is produced analogously to Example 5 with tert.-butylamine.

Yield: 35% of theory; m.p. 186° C. (from ethanol).

EXAMPLE 24

1-Ethyl-2-isopentylbiguanide Nitrate

This compound is prepared analogously to Example 5 with isopentylamine.

Yield: 13% of theory; m.p. 120°–122° C. (from acetonitrile).

EXAMPLE 25

1-Ethyl-2-cyclopentylbiguanide Nitrate

This compound is produced analogously to Example 5 with cyclopentylamine.

Yield: 13% of theory; m.p. 157°–158° C. (from water).

EXAMPLE 26

1,2-Di-n-propylbiguanide Nitrate ;

This compound is prepared analogously to Example 5 from 1-n-propyl-3-guanyl thiourea and n-propylamine.

Yield: 52% of theory; m.p. 137° C. (from acetonitrile).

EXAMPLE 27

1-n-Propyl-2-isopropylbiguanide Nitrate

The compound is produced analogously to Example 5 from 1-n-propyl-3-guanyl thiourea and isopropylamine.

Yield: 26% of theory; m.p. 178° C. (from ethanol).

EXAMPLE 28

2-Ethyl-1-p-chlorophenylbiguanide Nitrate

This compound is prepared in analogy to Example 5 with p-chloroaniline.

Yield: 18% of theory; m.p. 148°–149° C. (from acetonitrile).

EXAMPLE 29

2-Ethyl-1-p-chlorobenzylbiguanide Nitrate

This compound is produced analogously to Example 5 with p-chlorobenzylamine.

Yield: 25% of theory; m.p. 157°–158° C. (from ethanol).

EXAMPLE 30

2-Ethyl-1-β-phenethylbiguanide Nitrate

The compound is prepared analogously to Example 5 with β-phenethylamine.

Yield: 14% of theory; m.p. 118°–119° C. (from ethanol).

EXAMPLE 31

1-Ethyl-2-n-butylbiguanide Hydrochloride 29.3 g. (165 mmol) of 1-ethyl-3-guanyl thiourea carbonate is dissolved in the hot state in 300 ml. of ethanol and cooled to room temperature. Then, 33 ml. (330 mmol) of n-butylamine is added all at once thereto, and thereafter, within one-half hour, at maximally 30° C., a solution of 45 g. (165 mmol) of sublimate [mercuric chloride] in 150 ml. of ethanol is added dropwise thereto. The reaction mixture is agitated for 30 minutes at room temperature, the mercury sulfide is removed by centrifugation, and the alcoholic solution is concentrated to a syrupy consistency.

Under the addition of carbon, the mixture is recrystallized from 100 ml. of boiling acetonitrile.

Yield: 37% of theory; m.p. 132°–133° C. (from acetonitrile).

EXAMPLE 32

2-n-Butyl-1-p-chlorophenylbiguanide Nitrate

The compound is produced analogously to Example 5 from 1-n-butyl-3-guanyl thiourea carbonate and p-chlorophenylaniline.

Yield: 50% of theory; m.p. 156°–157° C. (from acetonitrile).

The 1-n-butyl-3-guanyl thiourea carbonate was prepared from butyl isothiocyanate and guanidine hydrochloride in accordance with methods known from the literature.

Yield: 33% of theory; m.p. 82°–83° C.

EXAMPLE 33

1-Ethyl-2-n-hexylbiguanide Hydrochloride 17.7 g. (100 mmol) of 1-ethyl-3-guanyl thiourea carbonate is dissolved in the hot state in 400 ml. of ethanol, mixed at 10° C. with 22.2 g. (220 mmol) of n-hexylamine, and cooled to 0°–5° C. At maximally 15° C. and within one hour, 38 g. (220 mmol) of silver nitrate in 1400 ml. of ethanol is added thereto, and the mixture stirred for 30 minutes at room temperature. Any excess silver ions are removed with hydrogen sulfide as the silver sulfide; the filtrate is concentrated to an oily consistency, dissolved in a small amount of water, and introduced into a column with 220 g. of a strongly basic anion exchanger (Ion Exchanger III, Merek AG.) in the OH⁻ form. The reaction product is eluted with 500 ml. of water, concentrated to dryness, and repeatedly concentrated to dryness in the presence of 100 ml. cyclohexane in order to remove any excess n-hexylamine. The resultant pure, free base of 1-ethyl-2-n-hexylbiguanide is converted into the hydrochloride with the stoichiometric amount of 1N hydrochloric acid; the hydrochloride is crystallized upon evaporation of the aqueous solution.

Yield: 23% of theory; m.p. 124°–125° C. (from acetonitrile).

EXAMPLE 34

1-Methyl-2-n-propylbiguanide Hydrochloride

This compound is prepared analogously to Example 33 from 1-methyl-3-guanyl thiourea carbonate and n-propylamine.

Yield: 29% of theory; m.p. 178°–179° C. (from ethanol).

EXAMPLE 35

1-Methyl-2-n-butylbiguanide Hydrochloride

The compound is produced analogously to Example 33 from 1-methyl-3-guanyl thiourea carbonate and n-butylamine.

Yield: 70% of theory; m.p. 134° C. (from isopropanol).

EXAMPLE 36

1-Methyl-2-n-hexylbiguanide Hydrochloride

This compound is produced analogously to Example 33 from 1-methyl-3-guanyl thiourea carbonate and n-hexylamine.

Yield: 13% of theory; m.p. 112°–113° C. (from acetonitrile).

EXAMPLE 37

1-Ethyl-2-allylbiguanide Hydrochloride

This compound is produced analogously to Example 33 with allylamine.

Yield: 34% of theory; m.p. 155°–156° C. (from isopropanol).

EXAMPLE 38

1-Allyl-2-cyclopropylbiguanide Hydrochloride

This compound is prepared analogously to Example 33 from 1-allyl-3-guanyl thiourea carbonate and cyclopropylamine.

Yield: 28% of theory; m.p. 164°–165° C. (from acetonitrile).

EXAMPLE 39

1-Ethyl-2-isopropylbiguanide Hydroiodide 9.2 g. (30 mmol) of 2-methyl-1-ethyl-3-guanyl isothiourea hydroiodide is agitated with 30 ml. of water and 11.8 g. (200 mmol) of isopropylamine for 48 hours at 30° C. and then for 2 hours at the boiling temperature. Excess isopropylamine, methyl mercaptan, and water are removed. To the oily residue, 2 ml. of concentrated aqueous sodium iodide solution and then water are added until a clear solution is obtained. The product is crystallized during standing in a refrigerator and is recrystallized from acetone-petroleum ether.

Yield: 3.05 g. = 32% of theory; m.p. 167°–168° C.

EXAMPLE 40

1-Methyl-2-ethylbiguanide Nitrate 2.52 g. (20 mmol) of 1-methyl-2-ethyl-3-cyanoguanidine, 1.76 g. (22 mmol) of ammonium nitrate, and 25 mg. of p-toluenesulfonic acid are heated under agitation for 48 hours in 15 ml. of dry nitrobenzene to 130° C. The cooled solution is extracted twice with respectively 25 ml. of water. The combined aqueous phases are extracted with ether, in order to remove any entrained nitrobenzene. The aqueous phase is evaporated to dryness and the resulting oil is dissolved in a small amount of hot ethanol. After standing for several days at room temperature, the 1-methyl-2-ethylbiguanide nitrate is crystallized.

Yield: 0.9 g. = 22% of theory; m.p. 140° C. (from methanol).

EXAMPLE 41

1,2-Diallylbiguanide Hydrochloride

The compound is produced analogously to Example 33 from 1-allyl-3-guanyl thiourea carbonate and allylamine.

Yield: 37% of theory; m.p. 147°–148° C. (from isopropanol).

EXAMPLE 42

2-Methyl-1,1-di-n-propylbiguanide Nitrate

This compound is obtained analogously to Example 5 from 1-methyl-3-guanyl thiourea carbonate and di-n-propylamine.

Yield: 40% of theory; m.p. 161°–162° C. (from acetonitrile).

EXAMPLE 43

1,1-Diethyl-2-n-propylbiguanide Nitrate

This compound is prepared analogously to Example 5 from 1-n-propyl-3-guanyl thiourea carbonate and diethylamine.

Yield: 17% of theory; m.p. 178°–179° C. (from ethanol).

EXAMPLE 44

1-Ethyl-2-n-heptylbiguanide Hydrochloride

The compound is prepared analogously to Example 33 with n-heptylamine.

Yield: 57% of theory; m.p. 122°–123° C. (from acetonitrile).

EXAMPLE 45

1-Methyl-2-n-heptylbiguanide Hydrochloride

The compound is prepared in analogy to Example 33 from 1-methyl-3-guanyl thiourea carbonate and n-heptylamine.

Yield: 65% of theory; m.p. 111°–112° C. (from acetonitrile).

EXAMPLE 46

1-Ethyl-2-n-pentylbiguanide Hydrochloride

This compound is produced analogously to Example 33 with n-pentylamine.

Yield: 15% of theory; m.p. 120°–121° C. (from acetonitrile)

EXAMPLE 47

1-Methyl-2-n-pentylbiguanide Hydrochloride

This compound is prepared analogously to Example 33 from 1-methyl-3-guanyl thiourea carbonate and n-pentylamine.

Yield: 30% of theory; m.p. 117°–118° C. (from acetonitrile : ethanol = 5 : 1).

EXAMPLE 48

2-Ethyl-1,1-pentamethylenebiguanide Nitrate

The compound is produced analogously to Example 5 with piperidine.

Yield: 33% of theory; m.p. 172° C. (from acetonitrile).

EXAMPLE 49

1-Methyl-2-cyclopropylbiguanide Hydrochloride

This compound is prepared analogously to Example 33 from 1-methyl-3-guanyl thiourea carbonate and cyclopropylamine.

Yield: 52% of theory; m.p. 183°–184° C. (from acetonitrile).

EXAMPLE 50

1-Methyl-2-allylbiguanide Hydrochloride

The compound is produced analogously to Example 33 from 1-methyl-3-guanyl thiourea carbonate and allylamine.

Yield: 61% of theory; m.p. 172°–173° C. (from isopropanol).

EXAMPLE 51

1-Propyl-2-allylbiguanide Hydrochloride

The compound is prepared in analogy to Example 33 from 1-n-propyl-3-guanyl thiourea carbonate and allylamine.

Yield: 51% of theory; m.p. 164°–166° C. (from acetonitrile).

EXAMPLE 52

2-Ethyl-1,1-di-n-pentylbiguanide Nitrate

The compound is produced analogously to Example 5 with di-n-pentylamine:

Yield: 58% of theory; m.p. 122°–123° C. (from water : isopropanol = 95 : 5).

EXAMPLE 53

1-Ethyl-2-n-octylbiguanide Hydrochloride

The compound is produced analogously to Example 33 with n-octylamine.

Yield: 35% of theory; m.p. 115°–116° C. (from acetonitrile).

EXAMPLE 54

2-Methyl-1,1-di-n-butylbiguanide Nitrate

The compound is produced analogously to Example 5 with di-n-butylamine.

Yield: 41% of theory; m.p. 122° C. (from acetonitrile).

EXAMPLE 55

1-n-Propyl-2-n-butylbiguanide Nitrate

The compound is prepared analogously to Example 5 from 1-n-propyl-3-guanyl thiourea carbonate and n-butylamine.

Yield: 21% of theory; m.p. 122°–123° C. (from acetonitrile).

EXAMPLE 56

2-Methyl-1,1-di-n-pentylbiguanide Nitrate

The compound is produced analogously to Example 5 from 1-methyl-3-guanyl thiourea carbonate and di-n-pentylamine.

Yield: 39% of theory; m.p. 137°–138° C. (from water).

EXAMPLE 57

1-Methyl-2-isopropylbiguanide Nitrate

The compound is produced analogously to Example 5 from 1-methyl-3-guanyl thiourea carbonate and isopropylamine.

Yield: 48% of theory; m.p. 137°–138° C. (from acetonitrile : isopropanol = 70 : 30).

EXAMPLE 58

2-Ethyl-1,1-tetramethylenebiguanide Nitrate

This compound is prepared analogously to Example 5 with pyrrolidine.

Yield: 28% of theory; m.p. 146°–147° C. (from ethanol).

EXAMPLE 59

2-Ethyl-1,1-dimethylenebiguanide Nitrate

This compound is produced analogously to Example 5 with aziridine.

Yield: 18% of theory; m.p. 161°–162° C. (from ethanol).

EXAMPLE 60

1-Ethyl-2-(2-methoxyethyl)-biguanide Hydrochloride

The compound is produced analogously to Example 33 with 2-methoxyethylamine.

Yield: 38% of theory; m.p. 124°–125° C. (from acetonitrile).

EXAMPLE 61

1-Ethyl-2-(3-methoxypropyl)-biguanide Hydrochloride

This compound is produced analogously to Example 33 with 3-methoxypropylamine.

Yield: 52% of theory; m.p. 119°–120° C. (from acetonitrile).

EXAMPLE 62

1-Methyl-2-(3-butoxypropyl)-biguanide Nitrate

The compound is prepared analogously to Example 5 from 1-methyl-3-guanyl thiourea carbonate and 3-n-butoxy-n-propylamine.

Yield: 65% of theory; m.p. 116°–117° C. (from acetonitrile).

EXAMPLE 63

1-Ethyl-2-(2-ethoxyethyl)-biguanide Hydrochloride

This compound is prepared analogously to Example 33 with 2-ethoxyethylamine.

Yield: 73% of theory; m.p. 84° C. (from acetonitrile-ether).

EXAMPLE 64

1-Ethyl-2-(6-methoxyhexyl)-biguanide Hydrochloride

The compound is produced in analogy to Example 33 with 6-methoxyhexylamine.

Yield: 60% of theory.

EXAMPLE 65

2-Ethyl-1,1-diethoxyethylbiguanide, Free Base

The compound is produced analogously to Example 33 with diethoxyethylamine. The aqueous solution of the free base, eluted from the ion exchanger, crystallizes upon concentration.

Yield: 37% of theory; m.p. 64°–68° C. (from acetonitrile).

EXAMPLE 66

1-Ethyl-2-n-butoxybiguanide Nitrate

This compound is prepared analogously to Example 5 with O-butylhydroxylamine.

Yield: 9% of theory; m.p. 174°–176° C. (from aqueous $NaNO_3$ solution).

EXAMPLE 67

1-Ethyl-2-trifluoroethylbiguanide Hydrochloride

The compound is prepared analogously to Example 33 with trifluoroethylamine hydrochloride.

Yield: 29% of theory; m.p. 184°–185° C. (from acetonitrile).

EXAMPLE 68

1-Ethyl-2-heptafluorobutylbiguanide Nitrate

This compounds is produced analogously to Example 5 with heptafluorobutylamine.

Yield: 45% of theory; m.p. 136°–139° C. (from acetonitrile).

EXAMPLE 69

2-Ethyl-1-methyl-1-trifluoroethylbiguanide Hydrochloride

The compound is produced analogously to Example 33 with methyltrifluoroethylamine.

Yield: 17% of theory.

EXAMPLE 70

1-Butyl-2-trifluoroethylbiguanide Hydrochloride

This compound is produced analogously to Example 33 from 1-butyl-3-guanyl thiourea carbonate and trifluoroethylamine.

Yield: 37% of theory; m.p. 144°–146° C. (from acetonitrile).

EXAMPLE 71

1-Methyl-2-heptafluorobutylbiguanide Nitrate

The compound is produced analogously to Example 5 from 1-methyl-3-guanyl thiourea carbonate and heptafluorobutylamine.

Yield: 22% of theory; m.p. 78°–80° C. (from chloroform).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A substituted biguanide of the formula

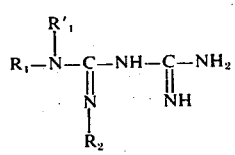

wherein $R_1$ is alkyl of 1–8 carbon atoms, $R'_1$ is hydrogen or alkyl of 1–8 carbon atoms and $R_2$ is alkoxyalkyl of 2–12 carbon atoms, and pharmaceutically acceptable acid addition salts thereof.

2. A substituted biguanide of the formula

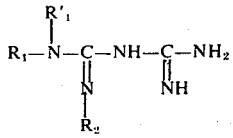

wherein $R_1$ is alkyl of 1–8 carbon atoms, $R'_1$ is hydrogen or alkyl of 1–8 carbon atoms and $R_2$ is fluorosubstituted alkyl of 1–12 carbon atoms and 1–8 fluorine atoms, and pharmaceutically acceptable acid addition salts thereof.

3. 1-Ethyl-2-n-butylbiguanide and pharmaceutically acceptable acid addition salts thereof.

4. The compound of claim 3, 1-ethyl-2-n-butylbiguanide hydrochloride.

5. The compound of claim 3, 1-ethyl-2-n-butylbiguanide.

6. A compound of claim 2 selected from the group consisting of 1-ethyl-2-trifluoroethylbiguanide hydrochloride, 1-ethyl-2-heptafluorobutylbiguanide nitrate, 2-ethyl-1-methyl-1-trifluoroethylbiguanide hydrochloride, 1-butyl-2-trifluoroethylbiguanide hydrochloride, and 1-methyl-2-heptafluorobutylbiguanide nitrate.

7. A compound of claim 1 selected from the group consisting of 1-ethyl-2-(2-methoxyethyl)-biguanide hydrochloride, 1-ethyl-2-(3-methoxypropyl)-biguanide hydrochloride, 1-methyl-2-(3-butoxypropyl)-biguanide nitrate, 1-ethyl-2-(2-ethoxyethyl)-biguanide hydrochloride, 1-ethyl-2-(6-methoxyhexyl)-biguanide hydrochloride, and 1-ethyl-2-n-butoxy-biguanide nitrate.

* * * * *